United States Patent [19]
Sommers et al.

[11] Patent Number: 5,693,401
[45] Date of Patent: Dec. 2, 1997

[54] SURGICAL GLOVE RETAINER

[75] Inventors: Jay Richard Sommers, Marietta; Corrine Ann Sukiennik, Alpharetta, both of Ga.

[73] Assignee: Kimberly-Clark Worldwide, Inc., Neenah, Wis.

[21] Appl. No.: 640,607

[22] Filed: May 1, 1996

[51] Int. Cl.⁶ .................................................. B32B 3/06
[52] U.S. Cl. .................. 428/100; 428/78; 428/99; 24/16 R; 24/442
[58] Field of Search ............... 428/100, 77, 78; 24/442, 16 R

[56] References Cited

U.S. PATENT DOCUMENTS

| | | | |
|---|---|---|---|
| 3,480,012 | 11/1969 | Smither et al. | 428/100 |
| 3,692,618 | 9/1972 | Dorschner et al. | 161/72 |
| 3,849,241 | 11/1974 | Butin et al. | 161/169 |
| 4,340,563 | 7/1982 | Appel et al. | 264/518 |
| 4,663,220 | 5/1987 | Wisneski et al. | 428/221 |
| 4,720,415 | 1/1988 | Vander Wielen et al. | 428/152 |
| 5,015,251 | 5/1991 | Cherubini | 24/16 R |
| 5,169,706 | 12/1992 | Collier, IV et al. | 428/152 |
| 5,226,992 | 7/1993 | Morman | 156/62.4 |
| 5,386,595 | 2/1995 | Kuen et al. | 24/442 |
| 5,501,697 | 3/1996 | Fisher | 606/204 |

FOREIGN PATENT DOCUMENTS

| 597852 | 4/1978 | Switzerland | 428/100 |
|---|---|---|---|

*Primary Examiner*—Alexander Thomas
*Attorney, Agent, or Firm*—Joseph P. Harps

[57] ABSTRACT

Disclosed is an elastic strip having a length which terminates at first and second generally opposed ends and a width which terminates at generally opposed edges. The strip has a first surface which includes an area of loops located near one of the opposed ends and a second surface which includes an area of hooks located near the other second opposed end. The strip is adapted to elongate and recover at least along the strip's length and the hooks are configured to engage the loops to join the first and second surfaces of the strip together. The device may be utilized to effect retention of a surgical glove in place upon the forearm of the wearer by encircling the wrist or forearm of the wearer of the surgical glove with the device, stretching the device about the gloved wrist/forearm and joining the opposed ends of the device about the gloved wrist/forearm. The device can be designed to be used only one time and then disposed. That is the device can be a "single use" device.

20 Claims, 2 Drawing Sheets ns, in many cases, can readily be transmitted from person to person as a result of contact with bodily fluids such as perspiration, blood, saliva, urine, menses and visceral fluids encountered by operating personnel during surgery, the medical industry has continuously sought out methods and equipment which serve to isolate the patient and operating personnel from each other in a manner that will lessen, if not eliminate, the likelihood of cross-contamination. That is to say, pathogens carried by the surgeon and/or other operating room personnel will not be given an opportunity to infect the patient. Likewise, the surgeon and operating room personnel desire not to come into contact with any adverse pathogens which may be borne by the patient and, in particular, the patient's bodily fluids. Over the last decade or so, this concern has been heightened significantly with the advent of the AIDS virus. Neither patients nor medical personnel wish to be exposed to a situation where the likelihood of cross-contamination is significant or, for that matter, exists at all.

5,693,401

SURGICAL GLOVE RETAINER

FIELD OF THE INVENTION

The field of the present invention is that of devices adapted to retain surgical gloves and the like in proper position.

BACKGROUND OF THE INVENTION

As modern medicine has advanced over the last century, the complexity of the surgical procedures which are performed by doctors on a routine basis has increased dramatically. The time was once when an operation lasting three or four hours was considered to be quite lengthy. Today, procedures lasting twelve to eighteen hours or even longer are encountered with growing frequency. Exemplary operations of this type are chemoreductive surgery where the surgeon has to work within the abdominal cavity to "work-in" chemotherapy agents for as long as eight to fourteen hours.

It is also well known that mankind's knowledge of the adverse affects of pathogens such as bacteria and viruses has increased astoundingly in modern times. Because these pathogens, in many cases, can readily be transmitted from person to person as a result of contact with bodily fluids such as perspiration, blood, saliva, urine, menses and visceral fluids encountered by operating personnel during surgery, the medical industry has continuously sought out methods and equipment which serve to isolate the patient and operating personnel from each other in a manner that will lessen, if not eliminate, the likelihood of cross-contamination. That is to say, pathogens carried by the surgeon and/or other operating room personnel will not be given an opportunity to infect the patient. Likewise, the surgeon and operating room personnel desire not to come into contact with any adverse pathogens which may be borne by the patient and, in particular, the patient's bodily fluids. Over the last decade or so, this concern has been heightened significantly with the advent of the AIDS virus. Neither patients nor medical personnel wish to be exposed to a situation where the likelihood of cross-contamination is significant or, for that matter, exists at all.

The medical industry has evolved a wide array of equipment to combat the problems associated with cross-contamination. For example, patients undergoing an operation typically wear a disposable gown and are covered with a surgical drape which is designed for the specific procedure which is to be conducted. Typically, the drape will have an aperture or slit in it through which the operation will take place. The drape is maintained within a sterile field until it is unpacked and placed upon the patient. This provides a first line of defense between the patient and operating personnel.

The surgeon or surgeons who are conducting the procedure along with other attendants who will be present in the operating room during the operation are provided with significant protection of their own. Such protection usually includes items such as garments or other items of wearing apparel which are designed to lessen or prevent the strike-through of the patient's bodily fluids through the garment and into contact with the surgeon or attendant which is the wearer. These items, which are designed to address any area which may be subject to attack by pathogen cross-contamination, include gowns, goggles, visors and gloves.

One of the problems which surgeons and operating room attendants have encountered in the use of surgical gloves during operations of extended length is that the gloves, which are typically pulled up over the cuff and sleeve of a gown, tend to roll down and create an avenue for pathogen cross-contamination.

An additional problem associated with the use of surgical gloves is that as a result of the gloves being pulled up over the cuff and sleeve of a gown a phenomenon known as "channelling" occurs. That is, the sleeve of the gown is bunched up underneath the glove as a result of the gathering effect the glove has as it is rolled up over the cuff and sleeve. The channels extend generally perpendicularly to the gathering force which is radial in nature. Thus, the channels typically extend along the length of the wearer's wrist beneath the glove. Channels extending in this direction are readily accessible to patient bodily fluids running down the outside of the sleeve of the gown which typically is fluid impervious. It is known that these fluids enter the channels and tend to work their way along the channels between the outer surface of fluid impervious gowns and the inner surface of the surgical glove. Those of skill in the art will readily recognize that this route allows the patient's bodily fluids to come into contact with the surgeon by contaminating the gown's cuffs which, typically, are absorbent and fluid pervious. This locus of contamination is of especial concern because, during long operations, the wrist is subject to almost constant movement. Frictional engagement between the surgeon's wrist and the cuff may result in minute abrasions which could complete the pathway for pathogen cross-contamination between the patient and the surgeon. This is highly undesirable.

Surgeons and other operating room attendants have attempted to address these problems in a crude fashion in at least two ways. Some surgeons and attendants have simply had someone else use adhesive tape to both tighten the fit of the gloves to close the channels and prevent roll down of the gloves. This approach has proven to be less than completely satisfactory because many of the common adhesives utilized in tapes are subject to attack by water and bodily fluids. Hence, the seal can be broken during the operation leaving the surgeon with a false sense of security. Others have simply had someone else stretch a rubber band open in circular fashion and have then inserted their hand through the opening and have had the rubber band be released. This procedure, likewise, has its drawbacks. Not the least of the drawbacks is the fact that it is an awkward and difficult procedure to conduct by the wearer. Additionally, it is very difficult to adjust the pressure asserted by the rubber band to assure a proper seal has occurred. To this end, a variety of rubber bands of different sizes and tensions needs to be maintained in stock.

From the above it is amply abundant that there exists a need for an improved device which both prevents glove roll-down, seals channels and is easy to use. Desirable commercial embodiments will be economically cost effective and, in all likelihood, disposable.

OBJECTS OF THE INVENTION

Accordingly, it is an object of the present invention to provide a device which is capable of preventing a surgical glove from rolling down a wearer's sleeve while the glove is in use.

It is a further object of the present invention to provide such a device which is easy to employ by the wearer of the glove.

It is yet another object of the present invention to provide such a device which may be retained about the wear by a hook and loop arrangement.

These and other objects and the broad scope of applicability of the present invention, will become apparent to those of skill in the art from the details given hereinafter. However, it should be understood that the detailed description of the presently preferred embodiments of the present invention is given only by way of illustration because various changes and modifications well within the spirit and scope of the invention will become apparent to those of skill in the art in view of this detailed description.

SUMMARY OF THE INVENTION

In response to the aforementioned difficulties encountered by those of skill in the art, we have invented an elastic strip having a length which terminates at first and second generally opposed ends and a width which terminates at generally opposed edges. The strip has a first surface which includes an area of loops located near one of the opposed ends and a second surface which includes an area of hooks located near the other second opposed end. The strip is adapted to elongate and recover at least along the strip's length and the hooks are configured to engage the loops to join the first and second surfaces of the strip together. The device may be utilized to effect retention of a surgical glove in place upon the forearm of the wearer by encircling the wrist or forearm of the wearer of the surgical glove with the device, stretching the device about the gloved wrist/forearm and joining the opposed ends of the device about the gloved wrist/forearm.

In some embodiments the elastic strip may have a length of from about 6 to 10 inches (15.25 to 25.5 cm). For example, the elastic strip may have a length of about 9.5 inches (24 cm). Furthermore, in some embodiments the elastic strip may have a width of from about 0.75 to 2 inches (1.9 to 5.1 cm). For example, the elastic strip may have a width of about 1 inch (2.54 cm).

In some embodiments, an area of one of the surfaces (first surface) of the elastic strip within at least 0.125 inch (0.3175 cm) of one of the opposed ends (first opposed end) of the strip configured to be devoid of loops. For example, the area of one of the surfaces (first surface) of the elastic strip within at least 0.250 inch (0.635 cm) of one of the opposed ends (first opposed end) of the strip is devoid of loops. Even more particularly, the area of one of the surfaces (first surface) of the elastic strip within at least 1 inch of one of the opposed ends (first opposed end) of the strip is devoid of loops.

In some embodiments, an area of the other surface (second surface) of the elastic strip within at least 0.125 inch (0.375 cm) of the other opposed end (second opposed end) of the elastic strip is devoid of hooks. For example, the area of the other surface (second surface) of the elastic strip within at least 0.250 inch (0.635 cm) of the other opposed end (second opposed end) is devoid of hooks. More particularly, the area of the other surface (second surface) of the elastic strip within at least 1 inch (2.54 cm) of the other opposed end (second opposed end) is devoid of hooks.

In some embodiments, an area of the first surface of the elastic strip within, at the most, 0.25 inch (0.635 cm) of both of the edges of the strip is devoid of loops.

In some embodiments, an area of the second surface of the elastic strip within, at the most, 0.25 inch (0.635 cm) of both edges of the strip is devoid of hooks.

The elastic strip may be formed from a wide variety of elastic materials. For example, the elastic strip may be formed from a stretch-bonded laminate. Alternatively, the elastic strip may be formed from a necked-bonded laminate. The material which provides the elastic strip with its elasticity may, in some embodiments, be a latex. In other embodiments, the material may be any non-latex elastomeric material.

In some embodiments, the elastic strip may be designed to be used only one time and then disposed. That is, the elastic strip may be designed to be a "single use" product.

DEFINITIONS

As used herein and in the claims the term "elastic" has its usual broad meaning. However, for purposes of the present invention, the term "elastic" may be conveniently defined as follows. A material is elastic if it is stretchable to an elongation of at least about 25 percent of its relaxed length, i.e., can be stretched to at least about one and one-quarter times its relaxed length, and, upon release of the stretching force, will recover at least about 40 percent of the elongation, i.e., will, in the case of 25% elongation, contract to an elongation of not more than 15%. For example, a 100 centimeter (cm) length of material will, under the foregoing definition, be deemed to be elastic if it can be stretched to a length of at least 125 centimeters and if, upon release of the stretching force, it contracts, in the case of being stretched to 125 cm, to a length of not more than about 115 centimeters. Of course, many elastic materials used in the practice of the present invention can be stretched to elongations considerably in excess of 25 percent of their relaxed length, and many, upon release of the stretching force, will recover to their original relaxed length or very close thereto. For example, the term "elastic" encompasses a material which is stretchable to an elongation of at least about 50 percent of its relaxed length, i.e., can be stretched to at least about one and one-half times its relaxed length, and, upon release of the stretching force, will recover at least about 90 percent of the elongation, i.e., will, in the case of 50% elongation, contract to a relaxed length not more than 105% of its original, relaxed length. At least for some purposes of the present invention, elastic materials which upon release of the stretching force recover all or nearly all of their elongation are desired.

As used herein, the term "nonelastic" means any material which does not meet the herein included definition of "elastic".

As used herein the term "stretch-bonded laminate" means a multilayer material having at least one elastic layer joined to at least one nonelastic gatherable layer at least at two spaced-apart locations in which the gatherable layer is gathered between the spaced-apart locations where it is joined to the elastic layer. The layers may be film layers, nonwoven web layers or layers of individual strands. A stretch-bonded laminate may be stretched (elongated) to the extent that the nonelastic gatherable material allows the elastic material to elongate without rupturing the nonelastic gatherable material. That is to say, a stretch-bonded laminate may be easily elongated to the point where the gathers of the gatherable layer are exhausted. At this point, further elongation of the stretch-bonded laminate can only occur by rupturing or otherwise physically deforming the nonelastic gatherable layer. Exemplary stretch-bonded laminates are disclosed in U.S. Pat. No. 4,720,415 to Vander Wielen et al. and U.S. Pat. No. 5,169,706 to Collier et al. The entirety of both of these patents is hereby incorporated by reference herein.

As used herein, the term "necked material" means any material which has been narrowed in at least one dimension by application of a tensioning force.

As used herein, the term "necked-bonded laminate" means any material having an elastic layer joined to a necked layer at least at two spaced-apart locations. The elastic layer may be joined to the necked layer at intermittent locations or may be completely bonded thereto. The joining is accomplished while the elastic layer and the necked layer are in juxtaposed configuration. The resultant necked-boned laminate is elastic in a direction generally parallel to the direction of neckdown (narrowing) of the necked material and may be stretched in that direction to the breaking point of the necked layer. A necked-bonded laminate may include more than two layers. For example, the elastic layer may have necked layers joined to both of its sides so that a three layer nicked-bonded laminate is formed having a structure of necked material/elastic layer/necked material. Additional elastic layers and/or necked layers may be added as desired. An exemplary patent discussing necked-bonded materials is U.S. Pat. No. 5,226,992 to Morman. The entirety of this patent is incorporated herein by reference.

As used herein, the term "palindromic laminate" means a multilayer laminate, for example, a necked-bonded laminate or a stretch-bonded laminate, which is substantially symmetrical in layer configuration. Exemplary palindromic laminates would have layer configurations of A/B/A, A/B/B/A, A/A/B/B/A/A, etc. Exemplary non-palindromic laminates would have layer configurations of A/B/C, A/B/C/A, A/C/B/D, etc.

As used herein, the term "polymer" generally includes, but is not limited to, homopolymers, copolymers, such as, for example, block, graft, random and alternating polymers, terpolymers, etc. and blends and modification thereof. Furthermore, unless otherwise specifically limited, the term "polymer" shall include all possible geometrical configurations of the material. These configurations include, but are not limited to, isotactic, syndiotactic and random symmetries.

As used herein, the term "consisting essentially of" does not exclude the presence of additional materials which do not significantly adversely affect the desired characteristics of a given composition or product. Exemplary materials of this sort would include, without limitation, pigments, antioxidants, stabilizers, surfactants, waxes, flow promoters, solvents, particulates and materials added to enhance processability of the composition.

As used herein, the term "nonwoven web" means a web having a structure of individual fibers or threads which are interlaid, but not in an identifiable, repeating manner. Nonwoven webs have been, in the past, formed by a variety of processes such as, for example, meltblowing processes, spunbonding processes and bonded carded web processes.

As used herein, the term "microfibers" means small diameter fibers having an average diameter not greater than about 100 microns, for example, having an average diameter of from about 0.5 microns to about 50 microns, or, more particularly, the microfibers may have an average diameter of from about 4 microns to about 40 microns. The average diameter is an average of five (5) separate measurements.

As used herein, the term "meltblown fibers" means fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed fibers. Such a process is disclosed, for example, in U.S. Pat. No. 3,849,241 to Buntin. The entire disclosure of this patent is hereby incorporated herein by reference.

As used herein, the term "spunbonded fibers" means small diameter fibers which are formed by extruding a molten thermoplastic material as filaments from a plurality of fine, usually circular, capillaries of a spinnerette with the diameter of the extruded filaments then being rapidly reduced as by, for example, eductive drawing or other well-known mechanisms. The production of spunbonded nonwoven webs is discussed in, for example, U.S. Pat. No. 4,340,563 to Appel et al. and U.S. Pat. No. 3,692,618 to Dorschner et al. the entirety of both of these patents is hereby incorporated by reference herein.

DETAILED DESCRIPTION OF THE INVENTION

Figure 1:
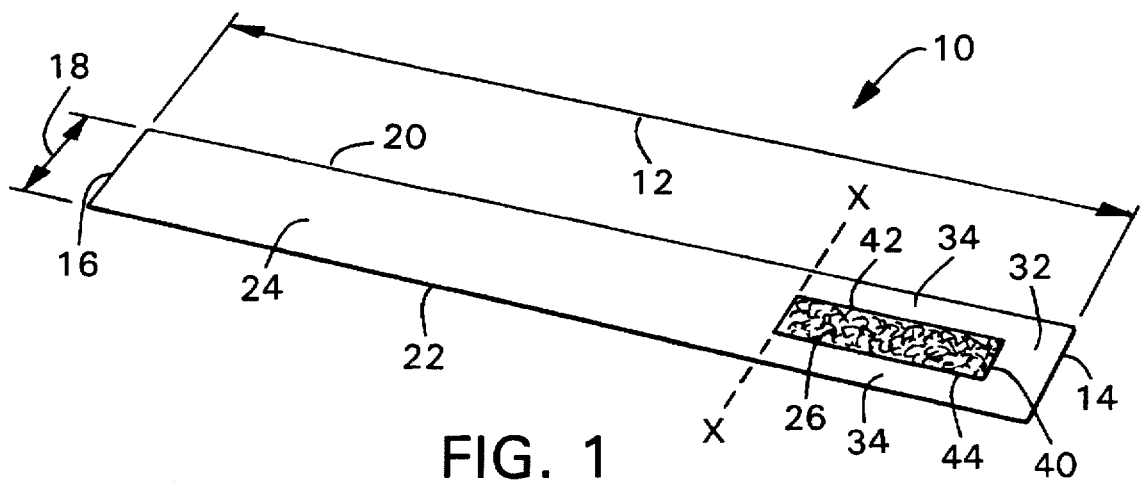
FIG. 1 is a schematic top plan view of an elastic strip formed in accordance with the teachings of the present invention.

Turning now to the drawings where like reference numerals represent like or equivalent structures or process steps, FIG. 1 illustrates an elastic strip 10 formed in accordance with the teachings of the present invention. The utility of the elastic strip 10 will become apparent to those of skill in the art. However, one of the uses for the elastic strip 10 is as a surgical glove retaining device as will be hereinafter described in detail.

The elastic strip 10 can be formed from a wide variety of elastic materials. Particular materials for forming the elastic strip 10 are stretch-bonded laminates and necked-bonded laminates. These materials and methods for their manufacture are well known to those of skill in the art. For purposes of explanation, an elastic strip 10 formed from a stretch-bonded laminate material will hereinafter be described.

FIG. 1 is a top plan view of the elastic strip 10 which discloses that the elastic strip 10 has a length dimension 12 which terminates at first and second opposed ends 14 and 16. The length 12 of the elastic strip 10 may vary from about six (6) to about ten (10) inches (15 to about 26 cm). For example, the length 12 of the elastic strip 10 may vary from about eight (8) to nine (9) inches (20 to about 23 cm). One desirable length 12 of the elastic strip 10 is about nine and one-half (9.5) inches (24 cm). The elastic strip 10 also has a width dimension 18 which terminates at first and second opposed edges 20 and 22. The width 18 of the elastic strip 10 may vary from about three-quarters (0.75) to two (2) inches (1.9 to about 5 cm). For example, the width 18 of the elastic strip 10 may vary from about three-quarter (0.75) to one and one-half (1.5) inches (1.9 to about 4 cm). One desirable width 18 of the elastic strip 10 is one (1) inch (2.54 cm). The elastic strip 10 also has a first surface 24 which includes an area of loops 26. The loops 26 are those of the conventional type of loops 26 known by those in the art for their use in conventional hook and loop fastening systems. These systems are marketed under the trademark VELCRO. The area of loops 26 can be formed by attaching a strip of appropriately sized conventional loop 26 material to the elastic strip 10. Attachment of the convention loop 26 material to the elastic strip 10 can be done in any conventional manner so long as the attachment mechanism does not interfere with the fastening function the loops 26 perform. One mechanism for attaching the strip of loop 26 material to the elastic strip 10 is by sewing. If the material which the elastic strip is formed from is loopy enough, that material may be satisfactory for performing the function of the loops 26 and separate attachment of loop 26 material can be dispensed with.

The area of loops 26 is located on the first surface 24 of the elastic strip 10 near the first opposed end 14. In many embodiments, the area of loops 26 can be bounded by the first opposed end 14, the opposed edges 20 and 22, and an imaginary line X—X which is generally perpendicular to the opposed edges 20 and 22 and spaced from the first opposed end 14 no more than about 20% of the length 12 of the elastic strip 10. Generally speaking, the area of loops 26 can take up all or any portion of the area defined by 14, 20, 22 and X—X. However, in some embodiments, it has been found to be desirable to recess the area of loops 26 inward from the first opposed end 14. In other embodiments, it has been found to be desirable to recess the area of loops 26 inward from the two opposed edges 20 and 22. In yet other embodiments, it has been found to be desirable to recess the area of loops 26 inward from both the first opposed end 14 and the two opposed edges 20 and 22. This latter configuration is illustrated in FIG. 1.

Figure 2:
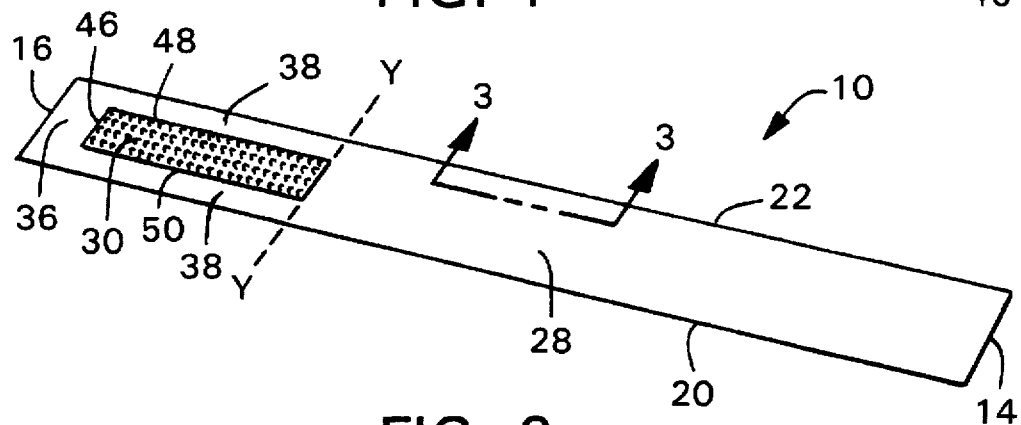
FIG. 2 is a schematic bottom plan view of the elastic strip of FIG. 1.

Turning to FIG. 2, which is a bottom plan view of the elastic strip 10, FIG. 2 illustrates that the elastic strip 10 has a second surface 28 which includes an area of hooks 30. The hooks 30 are those of the conventional type of hooks 30 known by those in the art for their use in conventional hook and loop fastening systems. As was previously stated, these systems are marketed under the trademark VELCRO. As was the case with the area of loops 26, the area of hooks 30 can be formed by attaching a strip of appropriately sized conventional hook 30 material to the elastic strip 10. Attachment of the convention hook 30 material to the elastic strip 10 can be done in any conventional manner so long as the attachment mechanism does not interfere with the fastening function the hooks 30 perform. One mechanism for attaching the strip of hook material 30 material to the elastic strip 10 is by sewing.

The area of hooks 30 is located on the second surface 28 of the elastic strip 10 near the second opposed end 16. In many embodiments, the area of hooks 30 can be bounded by the second opposed end 16, the opposed edges 20 and 22, and an imaginary line Y—Y which is generally perpendicular to the opposed edges 20 and 22 and spaced from the second opposed end 16 no more than about 20% of the length 12 of the elastic strip 10. Generally speaking, the area of hooks 30 can take up all or any portion of the area defined by 16, 20, 22 and Y—Y. However, in some embodiments, it has been found to be desirable to recess the area of hooks 30 inward from the second opposed end 16. In other embodiments, it has been found to be desirable to recess the area of hooks 30 inward from the two opposed edges 20 and 22. In yet other embodiments, it has been found to be desirable to recess the area of hooks 30 inward from both the second opposed end 16 and the two opposed edges 20 and 22. This latter configuration is illustrated in FIG. 2.

Turning back to FIG. 1, it can be seen that the recessing of the area of loops 26 from the first opposed end 14 results in the formation of area 32 which is loop 26 free. Additionally, the recessing of the area of loops 26 back from the opposed edges 20 and 22 results in the formation of loop 26 free areas 34. Likewise, review of FIG. 2 reveals that the recessing of the area of hooks 30 inward from the second opposed end 16, results in the formation of a hook 30 free area 36 and recessing of the area of hooks 30 inward from the opposed edges 20 and 22 results in the formation of hook 30 free areas 38.

As was just stated, recessing of the area of loops 26 and the area of hooks 30 inwardly from the respective first and second opposed ends 14 and 16 results in the formation of loop 26 free area 32 and hook 30 free area 36. These areas 32 and 36 function as fastener-free tab ends which, when the hooks 30 of the second surface 28 are engaged with the loops 26 of the first surface 24, extend somewhat above the plane of the joined first and second surfaces 24 and 28. As a result of this extension and the fact that the first and second surfaces 24 and 28 are not joined together in areas 32 and 36, the fastener-free tab ends of the elastic strip 10 are readily accessible to a wearer for separation of the connected first and second surfaces 24 and 28 and subsequent removal of the elastic strip 10 from about the wrist/forearm of a wearer when the elastic strip is used as a surgical glove retention device. Typically, the outboard edge 40 of the area of loops 26 will be recessed at least about one-eighth (⅛) of an inch (0.3175 cm) inwardly from the first opposed end 14. For example, the outboard edge 40 may be recessed at least about one-quarter (¼) of an inch (0.635 cm) inwardly from the first opposed end 14. In some embodiments, the outboard edge 40 may be recessed as much as one (1) inch inwardly from the first opposed end 14.

Typically, the lateral edges 42 and 44 of the area of loops 26 may be recessed at least about one-quarter (¼) inch inwardly from their respective opposed edges 20 and 22.

Typically, the outboard edge 46 of the area of hooks 30 will be recessed at least about one-eighth (⅛) of an inch (0.3175 cm) inwardly from the second opposed end 16. For example, the outboard edge 46 may be recessed at least about one-quarter (¼) of an inch (0.635 cm) inwardly from the second opposed end 16. In some embodiments, the outboard edge 46 may be recessed as much as one (1) inch inwardly from the second opposed end 16.

Typically, the lateral edges 48 and 50 of the area of hooks 30 may be recessed at least about one-quarter (¼) inch inwardly from their respective opposed edges 20 and 22.

Experimentation has discovered that recessing the lateral edges 42, 44, 48 and 50 inwardly about a quarter (¼) of an inch from their respective opposed edges 20 and 22 is an aid to the wearer in applying the elastic strip 10 when it is used as a surgical glove retention device. This recessed configuration results in improved juxtapositional alignment of the first surface 24 over the second surface 28. The resulting improved alignment of the edges 20 and 22 of the elastic strip 10 when it is used as a surgical glove retention device is desirable. Furthermore, the fact that the combined length of the areas of loops 26 and hooks 30 can be up to about 40% of the total length of the elastic strip 10 (20% plus 20%), allows the wearer to easily adjust the amount of tension the elastic strip 10 will exert on the wearer when the strip is used as a surgical glove retention device. Those of skill in the art will readily recognize that the tension exerted by the elastic strip 10 on the forearm/wrist of a wearer will increase as the effective length of the elastic strip 10 is reduced as the amount of overlap of the first and second surfaces 24 and 28 is increased and the circumference of the elastic strip in the connected configuration is reduced.

Figure 3:
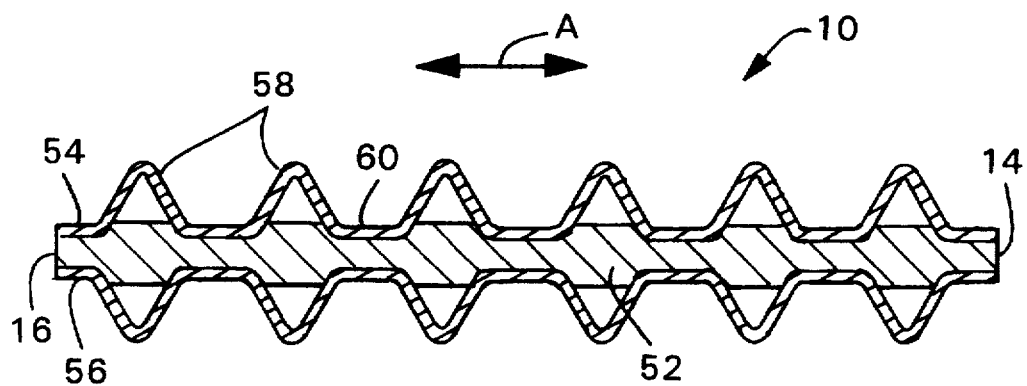
FIG. 3 is a highly magnified cross-sectional view of the elastic strip of FIG. 1 taken along line A—A in FIG. 2.

FIG. 3, which is a highly enlarged cross-sectional view of the elastic strip of FIG. 1 taken along line A—A of FIG. 2. FIG. 3 illustrates the structure of the elastic strip 10 when the strip is formed from a stretch-bonded laminate and, in particular a three layer stretch-bonded laminate. In that regard, FIG. 3 discloses that the stretch-bonded laminate elastic strip 10 has an inner elastic layer 52 and two outer nonelastic layers 54 and 56 formed from a gatherable material. The outer nonelastic layers 54 and 56 are in puckered-up (gathered) configuration when the stretch-bonded laminate 10 is in a relaxed (non-tensioned) state. These gathers 58 allow the stretch-bonded laminate 10 to extend in a direction generally perpendicular to the valleys 60 between the gathers 58. That is, the stretch-bonded laminate 10 can extend and retract along the direction generally indicated by the two-way arrow A in FIG. 3. This extension is limited by the gathers 58. When they are depleted, further extension is only possible if rupture or other physical rearrangement of the gatherable material occurs. Thus, the gathers, serve as a positive "stop" for the extension of the elastic strip 10.

The elastic layer 52 can be formed from any of a wide variety of elastic materials. For example, the elastic layer 52 may be formed from an elastomeric meltblown web formed from a blend of A-B-A' block copolymer(s) and polyolefin (s). Such webs are described in detail in U.S. Pat. No. 4,663,220 to Wisneski et al. and U.S. Pat. No. 4,720,415 to Vander Weilen. The subject matter of these patents is incorporated herein by reference in their entirety.

The gatherable layers 54 and 56 can be formed from any of a wide variety of gatherable materials. The characteristics necessary in the gatherable materials are that they be gatherable and that they offer a pleasing appearance, hand and drape qualities. That is, the gatherable material gives the elastic strip the touch and feel of a cloth-like item while still retaining the elastic function of the elastic inner layer 52. Exemplary materials from which the gatherable layer may be formed include a bonded carded polyester fiber web, a bonded carded polypropylene fiber web, a spunbonded polyester fiber web, a spunbonded polypropylene fiber web, cellulosic fiber webs, e.g. cotton webs, spunbond nylon webs sold under the trademark CEREX by Monsanto and blends of two or more of the foregoing.

The elastic strip 10 of the present invention can be utilized in a number of different ways. For example, the elastic strip 10 can be employed to prevent inadvertent "roll-down" of a surgical glove during its use. This application will be discussed in greater detail shortly. Additionally, the elastic strip 10 can be used to retain items in place. For example, it is envisioned that the elastic strip 10 could be used to retain intravenous lines in place and out of the way during a surgical procedure. In other embodiments, the elastic strip 10 could include a layer of conventional absorbent material. In such a situation, the elastic strip 10 could be used as a rapidly deployable bandage. Further embodiments in this area could include additionally layers containing conventional antiseptics and other wound healing aids. Bandages of this type could be quite useful in the treatment of burn patients.

Figure 4:
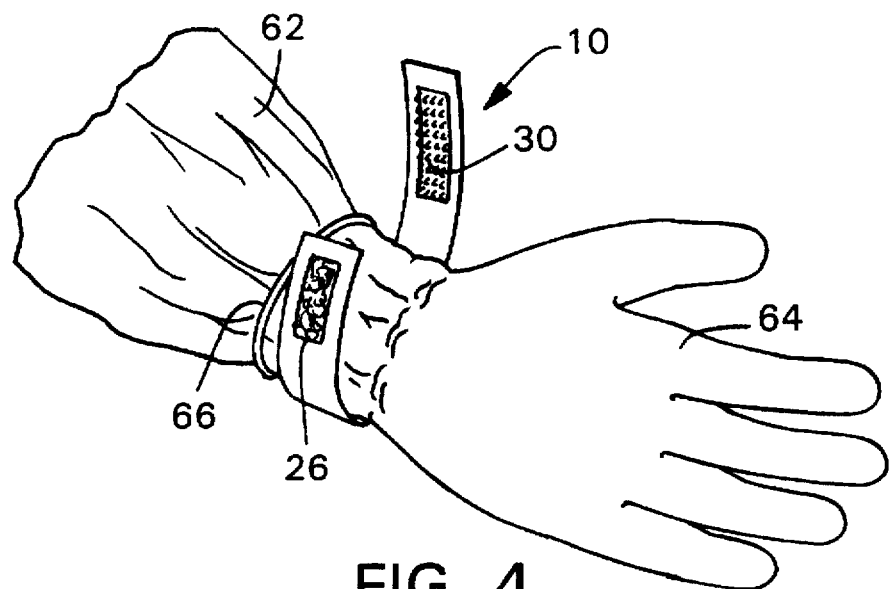
FIG. 4 is a portional view of a wearer's arm illustrating the application of an elastic strip formed in accordance with the present invention to an individual wearing a surgical gown and gloves.

Turning now to FIG. 4, there is illustrated a portional view of an individual limited the individual's arm, wrist and hand which is located within a conventional surgical gown 62. The individual is operating room personnel who must wear surgical gloves 64. Those of skill in the art know that most, if not all, surgical gloves 64 terminate with a wrist opening which is a thickened bead 66 of the material the glove is made from. The material is typically, a form of plastic or latex. Prior to an operation, a surgeon will don a garment 62 to protect his person from coming into contact with a patient's blood and other bodily fluids which may contain pathogens. The arm portion of the garment 62 typically terminates at or near the wrist of the surgeon with an elastic cuff which usually is designed to form an absorbent seal at the wrist region. Thereafter, the surgeon will don surgical gloves 64 and extend the wrist portion of the glove 64 over the wrist area of the garment 62 to form a complete protective barrier. As was discussed in the background of the invention, surgeons have experienced difficulties during long operations requiring extensive wrist/hand movements. These movements result, over a period of time, in the wrist portion of the surgical glove 64 slowly rolling down the wrist toward the surgeon's hand. This can result in a destruction of the protective barrier between the surgeon and the patient's bodily fluids. Additionally, even if the operation is not one which takes an extensive period of time and wrist/hand movements, the surgeon can be at risk due to the bunching up of the sleeve of the surgeon's garment underneath the glove 64. This bunching up results in the formation of small channels between the garment and glove 64 through which the patient's bodily fluids which have contacted the sleeve area of the garment 62 may flow. The thus flowing fluids can invade the protective barriers. This is quite unsatisfactory.

Figure 5:
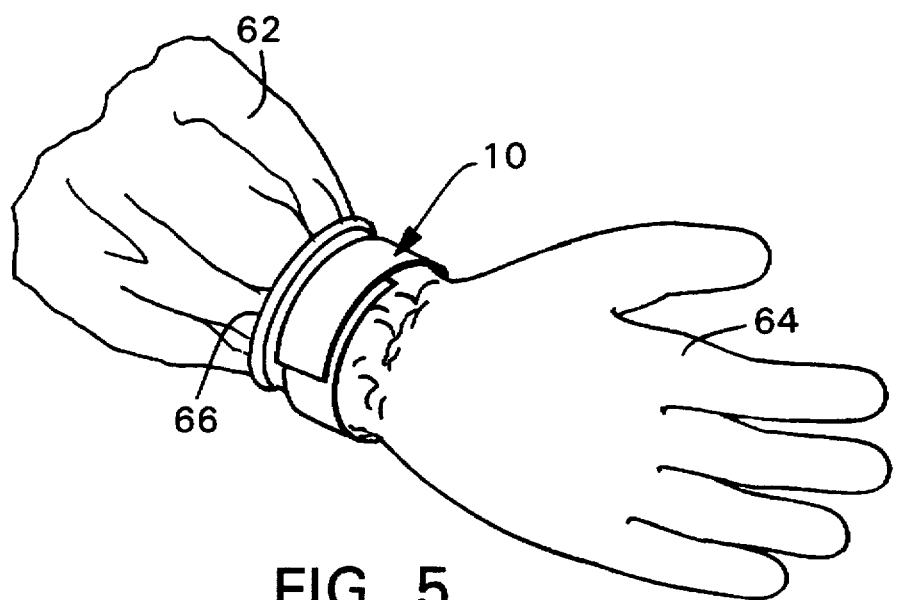
FIG. 5 is a portional view of a wearer's arm illustrating an elastic strip formed in accordance with the teachings of the present invention in position on the arm of an individual wearing a surgical gown and gloves.

FIG. 4 further illustrates an elastic strip 10 formed in accordance with the present invention being applied to a surgeon's or other appropriate wearer's forearm/wrist area over a surgical glove 64. In practice, the elastic strip 10 is stretched about the forearm/wrist area of the wearer and the hooks 30 of the second surface 28 are brought into contact with the loops 26 of the first surface 24 so as to retainingly engage the loops 26 of the first surface 24. The elastic strip 10 is then allowed to retract to a tight, yet non-restrictive, compressive fit about the forearm/wrist area of the wearer. This configuration is illustrated in FIG. 5. Because a hooks and loops arrangement is used to join the two surfaces 24 and 28 of the elastic strip 10 together, the surgeon can easily and quickly adjust the amount of compressive tensioning force applied by the elastic strip 10 to the forearm/wrist area. This arrangement has proven to be quite effective in preventing the "roll-down" of surgical gloves 64.

Figure 6:
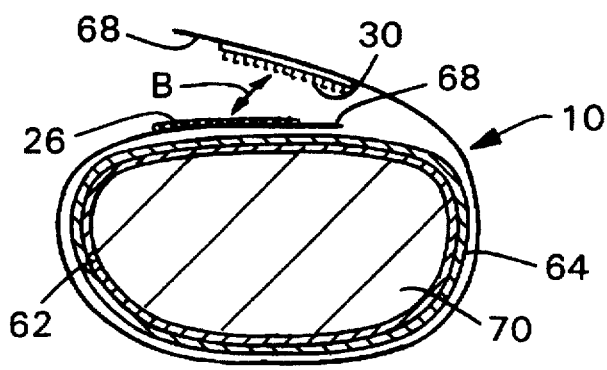
FIG. 6 is a schematic cross-sectional view demonstrating application of an elastic strip formed in accordance with the teachings of the present invention to a wearer's arm.

FIG. 6 offers further clarification of the elastic strip 10 in use as a surgical glove 64 retaining device. FIG. 6 is a schematic cross-sectional view of the arrangement illustrated in FIG. 4 with the cross-section being taken thorough the elastic strip 10, the surgical glove 64, the garment 62 and the surgeon's arm 70. This figure illustrates that the area of hooks 30 is extended over the area of loops 26 and brought into retaining engagement therewith through contact as indicated by the arrow B in FIG. 6. FIG. 6 also clearly indicates the presence of the fastener-free tab end 66 which allows the surgeon/wearer to readily grasp an end of the elastic strip 10 for its easy removal or adjustment. Reference to FIG. 6 demonstrates that the fastener-free tab end 68 is maintained slightly above the plane of the elastic strip 10 due to the thickness of the loops 26 and hooks 30. This arrangement further enhances the ability of a wearer to readily remove/adjust the elastic strip 10.

It is to be understood that variations and modifications of the present invention may be made without departing from the scope of the invention. It is also to be understood that the scope of the present invention is not to be interpreted as limited to the specific embodiments disclosed herein, but only in accordance with the appended claims when read in light of the foregoing disclosure.

What is claimed is:

1. An elastic strip having a length which terminates at first and second generally opposed ends and a width which terminates at generally opposed edges, the strip comprising:

a first surface comprising an area of loops located near the first opposed end in such a manner that an area of the first surface within at least 0.125 inch of the first opposed end is devoid of loops and an area of the first surface within, at the most, 0.25 inch of both edges is devoid of loops; and a second surface comprising an area of hooks located near the second opposed end in such a manner that an area of the second surface within at least 0.125 inch of the second opposed end is devoid of hooks and an area of the second surface within, at the most, 0.25 inch of both edges is devoid of hooks; and wherein the strip is adapted to elongate and recover at least along the strip's length and the hooks are configured to engage the loops to join the first surface of the strip to the second surface of the strip.

2. The elastic strip according to claim 1, wherein the strip has a length of from about 6 to 10 inches.

3. The elastic strip according to claim 2, wherein the strip has a length of about 9.5 inches.

4. The elastic strip according to claim 1, wherein the strip has a width of from about 0.75 to 2 inches.

5. The elastic strip according to claim 4, wherein the strip has a width of about 1 inch.

6. The elastic strip according to claim 1, wherein an area of the first surface within at least 0.250 inch of the first opposed end is devoid of loops.

7. The elastic strip according to claim 1, wherein an area of the first surface within at least 1 inch of the first opposed end is devoid of loops.

8. The elastic strip according to claim 1, wherein an area of the second surface within at least 0.250 inch of the second opposed end is devoid of hooks.

9. The elastic strip according to claim 8, wherein an area of the first surface within at least 0.250 inch of the first opposed end is devoid of loops.

10. The elastic strip according to claim 1, wherein an area of the second surface within at least 1 inch of the second opposed end is devoid of hooks.

11. The elastic strip according to claim 1, wherein an area of the first surface within, at the most, 0.250 inch of the first opposed end is devoid of loops.

12. The elastic strip according to claim 11, wherein an area of the second surface within, at the most, 0.250 inch of the second opposed end is devoid of hooks.

13. The elastic strip according to claim 1, wherein the area of loops has a length which is from 10–20 percent of the length of the strip.

14. The elastic strip according to claim 13, wherein the area of hooks has a length which is from 10–20 percent of the length of the strip.

15. The elastic strip according to claim 1, wherein the area of hooks has a length which is from 10–20 percent of the length of the strip.

16. A process for preventing roll-down of a surgical glove comprising the steps of:

donning a surgical gown having an arm portion which terminates at or near the wrist of the wearer with a cuff;

donning a surgical glove so that a wrist portion of the glove extends over the cuff of the surgical gown;

stretching the elastic strip of claim 1 about the wrist portion of the glove so that the hooks of the elastic strip retainingly engage the loops of the elastic strip;

allowing the elastic strip to retract to a compressive fit about the wrist portion of the glove.

17. An elastic strip of a stretch-bonded laminate having a length which terminates at first and second generally opposed ends and a width which terminates at generally opposed edges, the strip comprising:

a first surface comprising an area of loops located near the first opposed end in such a manner that an area of the first surface within at least 0.125 inch of the first opposed end is devoid of loops and an area of the first surface within, at the most, 0.25 inch of both edges is devoid of loops; and a second surface comprising an area of hooks located near the second opposed end in such a manner that an area of the second surface within at least 0.125 inch of the second opposed end is devoid of hooks and an area of the second surface within, at the most, 0.25 inch of both edges is devoid of hooks; and wherein the strip is adapted to elongate and recover at least along the strip's length and the hooks are configured to engage the loops to join the first surface of the strip to the second surface of the strip.

18. A process for preventing roll-down of a surgical glove comprising the steps of:

donning a surgical gown having an arm portion which terminates at or near the wrist of the wearer with a cuff;

donning a surgical glove so that a wrist portion of the glove extends over the cuff of the surgical gown;

stretching the elastic strip of claim 18 about the wrist portion of the glove so that the hooks of the elastic strip retainingly engage the loops of the elastic strip;

allowing the elastic strip to retract to a compressive fit about the wrist portion of the glove.

19. An elastic strip of a necked-bonded laminate having a length which terminates at first and second generally opposed ends and a width which terminates at generally opposed edges, the strip comprising:

a first surface comprising an area of loops located near the first opposed end in such a manner that an area of the first surface within at least 0.125 inch of the first opposed end is devoid of loops and an area of the first surface within, at the most, 0.25 inch of both edges is devoid of loops; and a second surface comprising an area of hooks located near the second opposed end in such a manner that an area of the second surface within at least 0.125 inch of the second opposed end is devoid of hooks and an area of the second surface within, at the most, 0.25 inch of both edges is devoid of hooks; and wherein the strip is adapted to elongate and recover at least along the strip's length and the hooks are configured to engage the loops to join the first surface of the strip to the second surface of the strip.

20. A process for preventing roll-down of a surgical glove comprising the steps of:

donning a surgical gown having an arm portion which terminates at or near the wrist of the wearer with a cuff;

donning a surgical glove so that a wrist portion of the glove extends over the cuff of the surgical gown;

stretching the elastic strip of claim 19 about the wrist portion of the glove so that the hooks of the elastic strip retainingly engage the loops of the elastic strip;

allowing the elastic strip to retract to a compressive fit about the wrist portion of the glove.

\* \* \* \* \*